United States Patent
Colbaugh (10) Patent No.: US 9,987,444 B2
(45) Date of Patent: Jun. 5, 2018

(54) SYSTEM AND METHOD FOR LIMITED FLOW RESPIRATORY THERAPY

(75) Inventor: Michael Edward Colbaugh, Level Green, PA (US)

(73) Assignee: Koninklijke Philips N.V., Eindhoven (NL)

(*) Notice: Subject to any disclaimer, the term of this patent is extended or adjusted under 35 U.S.C. 154(b) by 456 days.

(21) Appl. No.: 14/127,523

(22) PCT Filed: Jul. 31, 2012

(86) PCT No.: PCT/IB2012/053909
§ 371 (c)(1),
(2), (4) Date: Dec. 19, 2013

(87) PCT Pub. No.: WO2013/005201
PCT Pub. Date: Jan. 10, 2013

(65) Prior Publication Data
US 2014/0109910 A1    Apr. 24, 2014

Related U.S. Application Data

(60) Provisional application No. 61/503,634, filed on Jul. 1, 2011.

(51) Int. Cl.
*A61M 16/00* (2006.01)
*A61B 5/08* (2006.01)
(Continued)

(52) U.S. Cl.
CPC ....... *A61M 16/0051* (2013.01); *A61B 5/0826* (2013.01); *A61M 16/0057* (2013.01);
(Continued)

(58) Field of Classification Search
CPC .............. A61M 16/06; A61M 16/0666; A61M 16/205; A61M 2016/0027;
(Continued)

(56) References Cited

U.S. PATENT DOCUMENTS 5,458,137 A * 10/1995 Axe .......................... A61F 5/56
128/204.21
6,000,396 A * 12/1999 Melker ................. A61M 16/00
128/204.21
(Continued)

FOREIGN PATENT DOCUMENTS

AU         699726 B2    12/1998
CN        1901959 A     1/2007
(Continued)

OTHER PUBLICATIONS

Ian Colrain et al; "A Pilot Evaluation of a Nasal Expiratory Resistance Device for the Treatment of Obstructive Sleep Apnea", Journal of Clinical Sleep Medicine, vol. 4, No. 5, Oct. 1, 2008, pp. 426-433, XP055045280.

*Primary Examiner* — Todd J Scherbel
*Assistant Examiner* — Ned T Heffner (57) ABSTRACT

Methods and system of respiratory therapy treat sleep apnea by particular elevated pressure levels during the end of exhalation phases. Inhalation pressure levels may thus be significantly reduced and be, on average, lower than the exhalation pressure levels.

15 Claims, 7 Drawing Sheets

(51) Int. Cl.
    *A61M 16/16*     (2006.01)
    *A61M 16/06*     (2006.01)
    *A61M 16/08*     (2006.01)
    *A61B 5/087*     (2006.01)

(52) U.S. Cl.
    CPC .... *A61M 16/0069* (2014.02); *A61M 16/0666* (2013.01); *A61M 16/0875* (2013.01); *A61M 16/161* (2014.02); *A61B 5/087* (2013.01); *A61M 16/0009* (2014.02); *A61M 2016/0027* (2013.01); *A61M 2016/0039* (2013.01); *A61M 2205/332* (2013.01); *A61M 2205/3365* (2013.01); *A61M 2205/3368* (2013.01); *A61M 2205/3375* (2013.01); *A61M 2205/3569* (2013.01); *A61M 2205/3592* (2013.01); *A61M 2205/502* (2013.01); *A61M 2205/505* (2013.01); *A61M 2205/52* (2013.01); *A61M 2205/581* (2013.01); *A61M 2205/582* (2013.01); *A61M 2205/583* (2013.01)

(58) Field of Classification Search
    CPC .......... A61M 2205/50; A61M 2206/10; A61M 16/00–16/0012; A61M 16/0051–16/0075; A61M 16/16–16/168; A61M 16/20–16/207; A61M 16/0015–16/0042; A61M 39/00; A61M 39/10; A61B 5/00; A61B 5/0004; A61B 5/087–5/097; F16L 11/00–11/26
See application file for complete search history.

(56) References Cited

U.S. PATENT DOCUMENTS

| | | | |
|---|---|---|---|
| 2002/0043265 | A1 | 4/2002 | Barnett et al. |
| 2002/0185126 | A1* | 12/2002 | Krebs ................... A61M 16/12 128/200.24 |
| 2005/0166922 | A1 | 8/2005 | Knepper |
| 2007/0215146 | A1* | 9/2007 | Douglas ................ A61M 16/00 128/200.24 |
| 2008/0295839 | A1* | 12/2008 | Habashi ............ A61M 16/0051 128/204.22 |
| 2008/0302364 | A1* | 12/2008 | Garde ............... A61M 16/0045 128/204.23 |
| 2009/0301482 | A1 | 12/2009 | Burton et al. |
| 2009/0301488 | A1 | 12/2009 | Sun |

FOREIGN PATENT DOCUMENTS

| | | |
|---|---|---|
| CN | 101888868 A | 11/2010 |
| EP | 0661071 B1 | 2/2000 |
| JP | 2002543943 A | 12/2002 |
| JP | 2009511218 A | 3/2009 |
| WO | 9715343 A1 | 5/1997 |
| WO | 2007045017 A2 | 4/2007 |
| WO | 2009026582 A1 | 2/2009 |
| WO | 2010067236 A1 | 6/2010 |
| WO | 2010076711 A1 | 7/2010 |
| WO | 2010076712 A1 | 7/2010 |
| WO | 2010076713 A1 | 7/2010 |
| WO | 2011027243 A1 | 3/2011 |
| WO | 2011057362 A1 | 5/2011 |
| WO | 2012006339 A2 | 1/2012 |

\* cited by examiner

SYSTEM AND METHOD FOR LIMITED FLOW RESPIRATORY THERAPY

CROSS-REFERENCE TO PRIOR APPLICATIONS

This application is the U.S. National Phase application under 35 U.S.C. § 371 of International Application Serial No. PCT/IB2012/053909, filed on 31 Jul. 2012, which claims the benefit of U.S. Application Ser. No. 61/503,634, filed on 1 Jul. 2011. These applications are hereby incorporated by reference herein.

This application is related to U.S. Provisional Patent Application Ser. No. 61/244,113, entitled "SYSTEM AND METHOD FOR ENTRAINING THE BREATHING OF A SUBJECT," and filed Jul. 9, 2009. All of the related applications are hereby incorporated by reference into the present application in their entirety.

The present disclosure pertains to a system and method for treating sleep disorder breathing, and, in particular, for treating sleep apnea with limited flow respiratory therapy.

It is well known to treat sleep apnea with respiratory therapy, in particular traditional constant positive airway pressure (CPAP) therapies. Therapy adherence is commonly a challenge because traditional therapies may be uncomfortable for some patients. Specifically, breathing in while air is being forced into the airway using significant positive airway pressure may feel uncomfortable and/or unnatural to some patients.

Accordingly, it is an object of one or more embodiments to provide a system for treating sleep apnea of a subject and other disorders related to Sleep Disorder Breathing (SDB or "sleep disorder breathing"). The system includes a pressure generator, a timing module, and a control module. The pressure generator is configured to generate a pressurized flow of breathable gas for delivery to the airway of the subject. The timing module is configured to determine transitional moments that separate inhalation phases from exhalation phases and/or vice versa. The control module is configured to control the pressure generator to adjust pressure levels to provide inhalation pressure levels during inhalation phases and exhalation pressure levels during exhalation phases such that the average of the exhalation pressure levels is higher than the average of the inhalation pressure levels. The pressurized flow of breathable gas alternates, as does the breathing of a subject, between inhalation phases and exhalation phases that are separated by transitional moments.

It is yet another aspect of one or more embodiments to provide a method for treating sleep disorder breathing of a subject. The method comprises generating a pressurized flow of breathable gas for delivery to the airway of the subject; determining transitional moments that separate inhalation phases from exhalation phases and/or vice versa; and adjusting pressure levels of the pressurized flow, such that inhalation pressure levels are provided during inhalation phases and exhalation pressure levels are provided during exhalation phases. The average of the exhalation pressure levels is higher than the average of the inhalation pressure levels.

It is yet another aspect of one or more embodiments to provide a system configured to treat sleep disorder breathing. The system comprises means for generating a pressurized flow of breathable gas for delivery to the airway of the subject; means for determining transitional moments that separate inhalation phases from exhalation phases and/or vice versa; and means for adjusting pressure levels of the pressurized flow, such that inhalation pressure levels are provided during inhalation phases and exhalation pressure levels are provided during exhalation phases, wherein an average of the exhalation pressure levels is higher than an average of the inhalation pressure levels.

These and other objects, features, and characteristics of the present embodiments, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of any limits.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
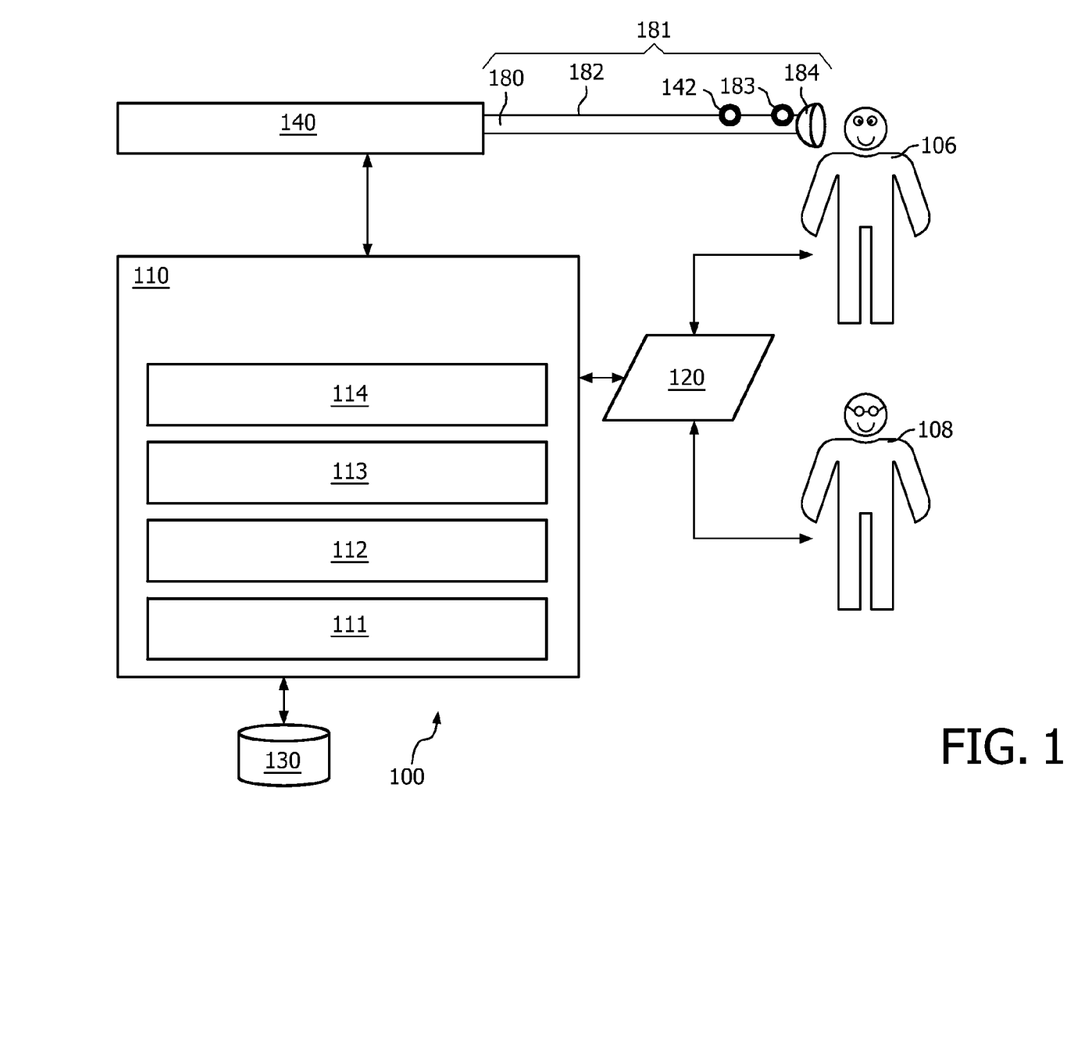
FIG. 1 schematically illustrates a system configured to treat sleep disorder breathing of a subject.

FIG. 1 schematically illustrates a system 100 configured to treat sleep disorder breathing of a subject. In particular, system 100 treats sleep disorder breathing, e.g. sleep apnea, by adjusting the pressure levels of a pressurized flow of breathable gas for delivery to the airway of a subject, e.g. in synchronization with the subject's natural breathing pattern and/or rate. Common respiratory treatments for sleep disorder breathing rely on constant positive airway pressure. One of the objectives of respiratory therapy may be to prevent collapse of the subject's airway. During unobstructed breathing, a subject alternately breaths in during an inhalation phase, and breathes out during an exhalation phase. A breath (or respiratory cycle) may comprise a cycle of one inhalation phase and one exhalation phase. An exhalation phase is usually at least as long as an inhalation phase, and may be two or more times longer than an inhalation phase. Common breathing rates for sleeping subjects range from eight to fifteen breaths per minute. Note that a subject's breathing rate may vary throughout a sleeping period. Inhalation phases and exhalation phases may be separated by transitional moments. System 100 may comprise one or more of a pressure generator 140, a processor 110, a sensor 142, an electronic storage 130, a user interface 120, a subject interface 180, and/or other constituent components.

Pressure generator 140 may be integrated, combined, coupled, or connected with a (positive) airway pressure device. Positive airway pressure therapy may deliver a pressurized flow of breathable gas to the airway of a subject, providing one or more inhalation pressure levels during the inhalation phase, and one or more exhalation pressure levels during the exhalation phase. Any pressure level during an inhalation phase may be referred to as an inhalation pressure level, though such a pressure level need not be constant throughout the inhalation phase. In addition to alternating between multiple levels, the inhalation pressure level may ramp up or down according to a predetermined slope (absolute and/or relative, e.g. dependent on breathing rate) for any specified section of a phase. Similar features may be available for exhalation phases. The pressure levels may be either predetermined and fixed, follow a predetermined dynamic characteristic, or they may dynamically change breath-to-breath or night-to-night depending on sensed breathing, breathing disorder, or other physiological characteristics. A diagram illustrating the airway pressure of a subject throughout one or more breaths may be referred to as a pressure profile diagram. For the purpose of defining, analyzing, comparing, and/or using a pressure profile diagram in some embodiments, mathematical operations including, but not limited to, statistical operations may be employed. For example, the average pressure level during a breathing phase may be determined.

Pressure generator 140 is configured to provide a pressurized flow of breathable gas to the airway of subject 106, e.g. via one or more gas delivery components 181. Subject 106 may or may not initiate one or more phases of respiration. Pressure support may be implemented as a higher and lower positive pressure of a (multi-level) PAP device. For example, to support inspiration, the pressure of the pressurized flow of breathable gas may be adjusted to an Inspiratory Positive Air Pressure (IPAP). Alternatively, and/or simultaneously, to support expiration, the pressure of the pressurized flow of breathable gas may be adjusted to an Expiratory Positive Air Pressure (EPAP). Other schemes for providing respiratory support (including CPAP, BiPAP®, and/or other schemes) through the delivery of the pressurized flow of breathable gas are contemplated.

An airway pressure device may be configured such that one or more gas parameters of the pressurized flow of breathable gas are controlled in accordance with a therapeutic respiratory regimen for subject 106. The one or more gas parameters include one or more of flow, volume, retrograde volume, pressure, humidity, velocity, acceleration, (intentional) gas leak, and/or other parameters. System 100 may be configured to provide types of therapy including types of therapy where a subject performs inspiration and/or expiration of his own accord or where the device provides negative airway pressure.

A pressurized flow of breathable gas may be delivered from pressure generator 140 to or near the airway of subject 106 via one or more gas delivery components 181, which may include, e.g., a subject interface 180. Subject interface 180 may include a conduit 182, a subject interface appliance 184, and/or other components, any of which may be considered gas delivery components 181. Conduit 182 may be a flexible length of hose, or other conduit, that places subject interface appliance 184 in fluid communication with pressure generator 140. Conduit 182 may include a flow resistor 183. Conduit 182 forms a flow path through which the pressurized flow of breathable gas is communicated between subject interface appliance 184 and pressure generator 140. Conduit 182 may comprise a standard 22 mm diameter hose (other common diameters range between ¾" and 1") or, in certain embodiments, a much smaller diameter hose that is in the range of ⅓ of a standard size hose. Such a hose, which may be referred to as a restricted flow hose or limited flow hose, (for example, having a diameter ranging between ¼" and ⅓", or alternatively between 6 mm and 9 mm) has a greater resistance to gas flow and allows/requires a lower peak flow, typically of less than 50% compared to a standard size hose (in some embodiments between 20%-30% of the peak flow through a standard size hose). Less flow and less energy are required when using a smaller hose to operate the system, in a manner described herein, to treat respiratory events. Additionally, such a system may be smaller and/or less obtrusive.

Subject interface appliance 184 is configured to deliver the pressurized flow of breathable gas to the airway of subject 106. As such, subject interface appliance 184 may include any appliance suitable for this function. In certain embodiments, pressure generator 140 is a dedicated ventilation device and subject interface appliance 184 is configured to be removably coupled with another interface appliance being used to deliver respiratory therapy to subject 106. For example, subject interface appliance 184 is configured to engage with and/or be inserted into an endotracheal tube, a tracheotomy portal, and/or other interface appliances. In certain embodiments, subject interface appliance 184 is configured to engage the airway of subject 106 without an intervening appliance. In this embodiment, subject interface appliance 184 includes one or more of an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present disclosure is not limited to these examples, and contemplates delivery of the pressurized flow of breathable gas to subject 106 using any subject interface.

Figure 2:
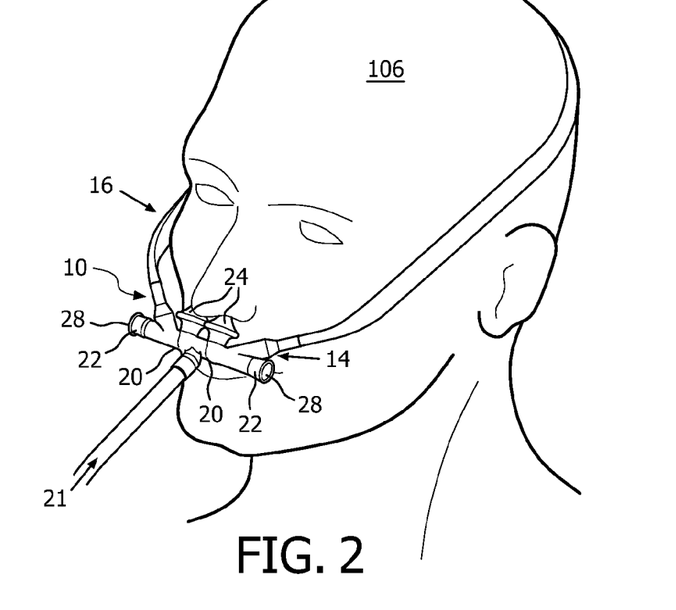
FIG. 2, 3 illustrate a subject interface appliance configured to provide respiratory therapy.

By way of illustration, FIG. 2 illustrates an exemplary subject interface appliance 10 configured to provide respiratory therapy. Subject interface appliance 10 may be used in place of subject interface appliance 184 (as shown in FIG. 1) to deliver the pressurized flow of breathable gas to subject 106, e.g. via a restricted flow hose 21. Subject interface appliance 10 restricts the exhalation of subject 106, e.g. to support the generation of the desired pressure profile. In one embodiment, subject interface appliance 10 includes one or more bodies 14 that enclose one or more external orifices (e.g., nostrils) of the airway of subject 106, and a fastener 16. Fastener 16 holds body 14 in place over the one or more external orifices of the airway of subject 106. In the embodiment shown in FIG. 2, fastener 16 is a single strap that loops around the head of subject 106. In one embodiment, fastener 16 includes a headgear having a different configuration for engaging the head of fastener 16 to hold body 14 in place. In one embodiment, fastener 16 includes a structure that engages the interior of the one or more openings of the airway of subject 106, and/or an adhesive that attaches to the skin of subject 106 to hold body 14 in place. In some instances (not shown), subject interface appliance 10 may be implemented and/or formed integrally with an oral appliance and/or headgear that holds the lower jaw of subject 106 in a position that opens the airway of subject 106 (e.g., with the lower jaw extended forward), and/or holds the mouth of subject 106 closed to encourage breathing through the nostrils.

Figure 3:
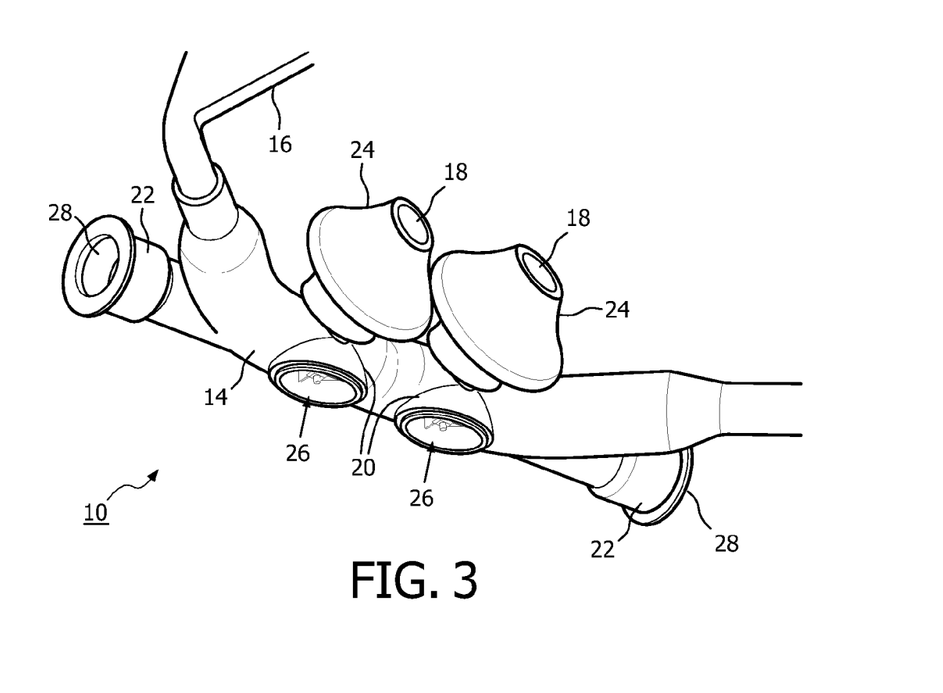

By way of further illustration, FIG. 3 shows an enlarged view of body 14. Body 14 forms a plurality of openings with flow paths therebetween. In one embodiment, the interior of body 14 is hollow, and without substantial impediment to the flow of gas from any of the various openings to any of the other various openings. The plurality of openings may include one or more subject interface openings 18, a set of inhalation ports 20, a set of exhalation ports 22, and an interface to pressure generator 140 (not shown). The subject interface openings 18 communicate gas within the flow paths formed inside of body 14 with the airway of subject 106. As will be described further below, body 14 forms a first subset of flow paths between inhalation ports 20 and subject interface openings 18 that deliver gas from e.g. ambient atmosphere to the one or more external orifices of the airway of subject 106 during inhalation. Body 14 forms a second subset of flow paths between exhalation ports 22 and subject interface openings 18 that deliver gas from the one or more external orifices of subject 106 to e.g. ambient atmosphere during exhalation.

In one embodiment, subject interface openings 18 are formed by airway enclosing members 24. FIG. 3 depicts airway enclosing members 24 as nasal pillows that enclose the nostrils of subject 106. Airway enclosing members 24 may be selectably detachable from the rest of body 14. This will facilitate cleaning and/or replacement of airway enclosing members 24 for hygienic purposes, and/or selection of airway enclosing members 24 by subject 106 based on personal preference (e.g., from members having different sizes, different sized openings, etc.).

At the set of inhalation ports 20, subject interface appliance 10 includes a set of inhalation valves 26. Inhalation valves 26 may permit gas to flow relatively freely from e.g. ambient atmosphere into the flow paths formed within body 14 through inhalation ports 20, but significantly resist or seal the flow of gas from within body 14 to e.g. ambient atmosphere through inhalation ports 20. For example, inhalation valves 26 may be "one way" valves that permit gas to flow freely into body 14 from atmosphere, but block gas within body 14 from flowing externally. As such, during inhalation, the flow paths formed within body between inhalation ports 20 and subject interface openings 18 allow gas to be drawn freely from inhalation ports 20 to subject interface openings 18 and into the nostrils of subject 106. However, during exhalation, inhalation valves 26 significantly resist or seal the flow of exhaled gas from the nostrils of subject 106 to ambient atmosphere through the first subset of flow paths formed within body 14 from subject interface openings 18 to inhalation ports 20. In one embodiment, inhalation valves 26 are selectably detachable from the rest of body 14. This facilitates cleaning of valves 26 and/or body 14, and may enable valves 26 to be replaced for hygienic purposes, or if one of inhalation valves 26 stops functioning correctly. The inhalation valves may alternatively be incorporated into the hose or other part of the system's air circuit.

At the set of exhalation ports 22, subject interface appliance 10 includes a set of exhalation valves 28. Exhalation valves 28 regulate the flow of gas between the nostrils of subject 106 and e.g. ambient atmosphere within the second subset of flow paths formed inside body 14 between subject interface openings 18 and exhalation ports 22. In particular, exhalation valves 28 provide a resistance to the flow of gas from the nostrils of subject 106 to e.g. ambient atmosphere in the second subset of flow paths during exhalation. The resistance provided by exhalation valves 28 to these flows of exhaled gas primarily characterize a cumulative resistance of subject interface appliance 10 to gas being exhaled from the nostrils of subject 106. In fact, if inhalation valves 26 seal inhalation ports 20 against gas flow from within body 14 to ambient atmosphere, then the cumulative resistance of exhalation valves 28 to the flow of gas exhaled through the nostrils of subject 106 to atmosphere is the cumulative resistance of respiration appliance to gas exhaled from the nostrils of subject 106. It is helpful to note that the combined flow from the patient plus the flow from a pressure/flow generator produces the desired mask pressure. These combined flows generate a pressure because of the exhalation resistance (assuming subject interface leak is zero, and the pressure level generated by the pressure generator exceeds that the pressure level inside the mask). The pressure generator may dynamically reduce the effective exhalation resistance by reducing its (output) pressure level to a value less than that the pressure level inside the mask. In this case, patient exhalation flow is free to split between the exhalation resistor and down the hose. The patient exhalation resistance is a parallel combination of the exhalation resistor and the hose resistance (taking into account the differential pressures on either side of the resistances). The effective combined resistance to patient exhalation can in this way be reduced. Appropriate control of the pressure level generated by the pressure generator during the respiratory cycle may be used for mask pressure regulation, patient comfort, and/or other purposes.

Referring back to FIG. 1, system 100 may include electronic storage 130 comprising electronic storage media that electronically stores information. The electronic storage media of electronic storage 130 includes one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 130 stores software algorithms, information determined by processor 110, information received via user interface 120, and/or other information that enables system 100 to function properly. For example, electronic storage 130 may record or store timing information (including duration of inhalation phases and exhalation phases as well as transitional moments), one or more (breathing) parameters and/or other parameters (as discussed elsewhere herein), pressure levels, information indicating whether the subject adequately complied with a prescribed respiratory therapy regimen, information indicating whether a respiratory event (including Cheyne-Stokes respiration, central sleep apnea, obstructive sleep apnea, hypopnea, snoring, hyperventilation, and/or other respiratory events) occurred, information indicating adequacy of treatment, and/or other information. Electronic storage 130 may be a separate component within system 100, or electronic storage 130 may be provided integrally with one or more other components of system 100 (e.g., processor 110).

User interface 120 is configured to provide an interface between system 100 and a user (e.g., user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information is e.g. provided to subject 106 by user interface 120 in the form of auditory signals, visual signals, tactile signals, and/or other sensory signals.

By way of non-limiting example, in certain embodiments, user interface 120 includes a radiation source capable of emitting light. The radiation source includes one or more of an LED, a light bulb, a display screen, and/or other sources. User interface 120 controls the radiation source to emit light in a manner that conveys to subject 106 information related to breathing and/or the pressurized flow of breathable gas. Note that the subject and the user of system 100 may be the same person.

It is to be understood that other communication techniques, either hard-wired or wireless, are also contemplated herein as user interface 120. For example, in one embodiment, user interface 120 is integrated with a removable storage interface provided by electronic storage 130. In this example, information is loaded into system 100 from removable storage (e.g., a smart card, a flash drive, a removable disk, etc.) that enables the user(s) to customize the implementation of system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

Sensor 142 is configured to generate one or more output signals conveying measurements related to the respiration of subject 106. The measurements may relate to gas parameters and/or other parameters. Gas parameters may include flow, pressure, humidity, velocity, acceleration, and/or other gas parameters related to the pressurized flow of breathable gas delivered to subject 106. Output signals may convey measurements related to respiratory parameters. Sensor 142 may be in fluid communication with conduit 182 and/or subject interface appliance 184.

The illustration of sensor 142 as including a single member in FIG. 1 is not intended to be limiting. In certain embodiments sensor 142 includes a plurality of sensors operating as described above by generating output signals conveying information related to parameters associated with the gas breathed by subject 106 and/or the delivery of the gas to subject 106. Alternatively, and/or simultaneously, a breathing parameter may be related to a mechanical unit of measurement of a component of system 100 such as rotor speed, motor speed, blower speed, fan speed, or a related measurement that serves as a proxy for any of the previously listed breathing parameters through a previously known/calibrated mathematical relationship. Resulting signals or information from sensor 142 may be transmitted to processor 110, user interface 120, electronic storage 130, and/or other components of system 100. This transmission can be wired and/or wireless.

Processor 110 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 includes a plurality of processing units.

As is shown in FIG. 1, processor 110 is configured to execute one or more computer program modules. The one or more computer program modules include one or more of a timing module 111, a parameter determination module 112, a control module 113, a respiratory event module 114, and/or other modules. Processor 110 may be configured to execute modules 111, 112, 113, and/or 114 by software; hardware; firmware; some combination of software, hardware, and/or firmware; and/or other mechanisms for configuring processing capabilities on processor 110.

It should be appreciated that although modules 111, 112, 113, and 114 are illustrated in FIG. 1 as being co-located within a single processing unit, in implementations in which processor 110 includes multiple processing units, one or more of modules 111, 112, 113, and/or 114 may be located remotely from the other modules. The description of the functionality provided by the different modules 111, 112, 113, and/or 114 described below is for illustrative purposes, and is not intended to be limiting, as any of modules 111, 112, 113, and/or 114 may provide more or less functionality than is described. For example, one or more of modules 111, 112, 113, and/or 114 may be eliminated, and some or all of its functionality may be provided by other ones of modules 111, 112, 113, and/or 114. Note that processor 110 may be configured to execute one or more additional modules that may perform some or all of the functionality attributed below to one of modules 111, 112, 113, and/or 114.

Timing module 111 is configured to determine transitional moments that separate inhalation phases from exhalation phases and/or vice versa. This determination may be based on output signals from sensor 142. For example, a transitional moment that separates an inhalation phase from an exhalation phase may be determined by analyzing the direction, amount, and/or rate of flow of breathable gas in or out of the airway of subject 106. Note that functionality attributed to timing module 111 may be incorporated into other constituent components of system 100.

Parameter determination module 112 is configured to determine one or more gas parameter, breathing parameters, and/or other parameters from the output signals generated by sensor(s) 142. Gas parameters of the (pressurized) flow of breathable gas may include one or more of (peak) flow, pressure, temperature, humidity, velocity, acceleration, gas composition (e.g. concentration(s) of one or more constituents), thermal energy dissipated, (intentional) gas leak, and/or other gas parameters related to the (pressurized) flow of breathable gas. Breathing parameters may be derived from the one or more gas parameters, and include one or more of tidal volume of the breathing of the subject, retrograde volume, respiratory rate, breathing period, inhalation time or period, exhalation time or period, peak flow, flow rate of the breathing of the subject, respiration flow curve shape, transition time from inhalation to exhalation and/or vice versa, transition time from peak inhalation flow rate to peak exhalation flow rate and/or vice versa, respiration pressure curve shape, (intentional) gas leak, and/or other breathing parameters. Parameter determination module 112 may use signals and/or information from timing module 111 during operation, e.g. to determine inhalation period, inhalation volume, and/or inhalation flow rate. Some or all of the stated functionality of parameter determination module 112 may be incorporated or integrated into other computer program modules of processor 110.

Control module 113 is configured to control pressure generator 140 to adjust pressure levels for system 100. Control module 113 may be configured to control pressure generator 140 to provide the pressurized flow of breathable gas at inhalation pressure levels during inhalation phases, and at exhalation pressure levels during exhalation phases. Control module 113 may be configured to adjust pressure levels of the pressurized flow of breathable gas such that exhalation pressure levels are generally higher than inhalation pressure levels. For example, exhalation pressure levels may be generally higher than inhalation pressure levels during a given duration of time and/or number of breaths. The given duration of time and/or number of breaths may include, for example, two or more consecutive respiratory phases, multiple breaths, a period corresponding to a predetermined amount of time (a second, 10 seconds, a minute, an hour, etc.), and/or for other durations of time. Exhalation pressure levels that are generally higher than inhalation pressure may refer, for example, to average exhalation pressure levels that are higher than average inhalation pressure levels, the median exhalation pressure level for a set of exhalation pressure levels may be higher than the median inhalation pressure level for a set of inhalation pressure levels, and/or levels of other metrics related to the pressure level at or near the airway of the subject may correspond to greater pressure during exhalation than during inhalation. Parameters determined by parameter determination module 112 and/or timing module 111 may be used by control module 113 in a feedback manner to adjust system settings/operations.

Figure 4:
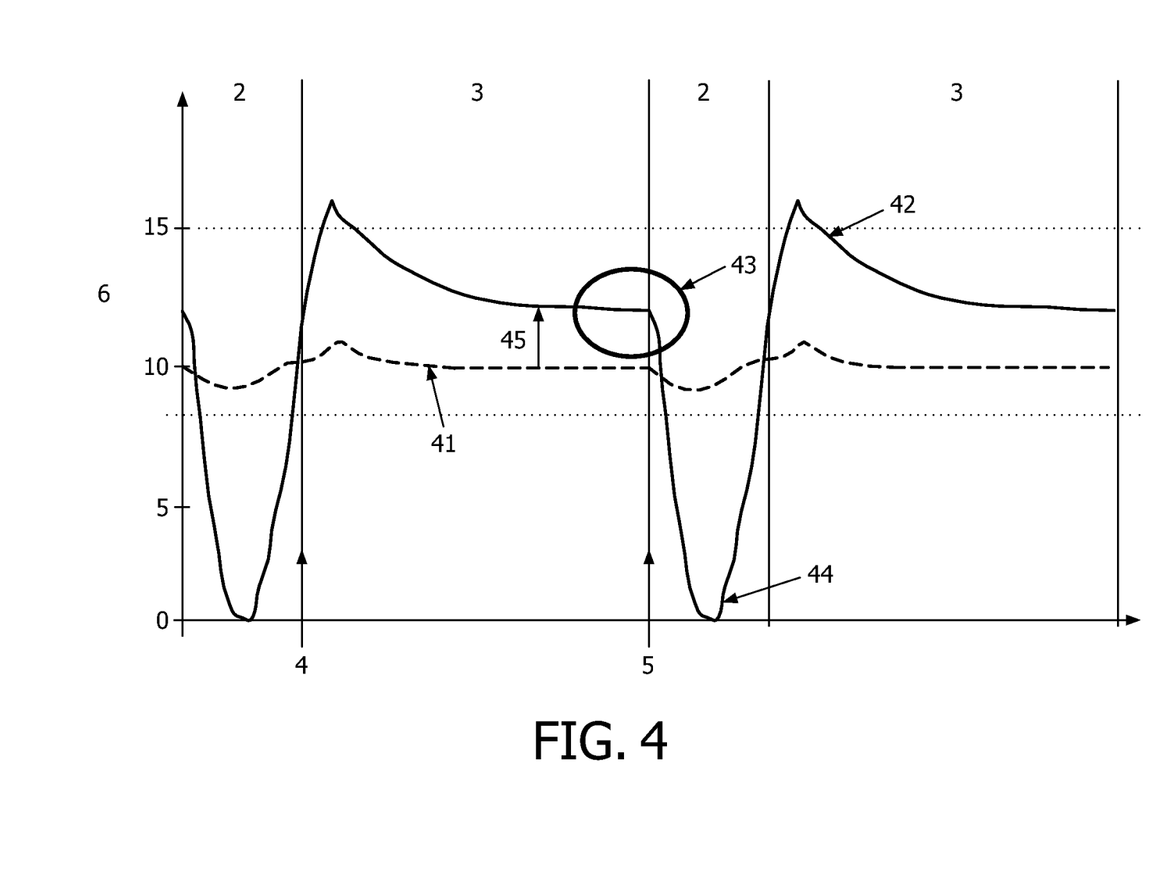
FIGS. 4, 5, 6, and 7 illustrate pressure profile diagrams that exemplify the operation of certain embodiments disclosed herein (note: independent axis represents time, and dependent axis represents mask pressure)

Control module 113 may be configured to time its operations relative to the transitional moments determined by timing module 111. By way of illustration, FIG. 4 illustrates a pressure profile diagram 42 in which inhalation phases 2 are separated from exhalation phases 3 by transitional moment 4 (for a transition from inhalation phase to exhalation phase) and transitional moment 5 (for a transition from exhalation phase 3 to inhalation phase 2). Control module 113 may be configured to adjust the pressure as follows: During the final 0.25 seconds (or, alternatively, 0.5 seconds, 1.0 seconds, 1.5 seconds, or 2.0 seconds) of an exhalation phase, the exhalation pressure level may be held substantially constant at a pressure level that is elevated from a pressure level that is expected to adequately treat, e.g., sleep apnea using constant positive airway pressure therapy by a predetermined amount of pressure. Instead of using an absolute duration at the end of the exhalation phase, adjustments of the exhalation pressure level may be held substantially constant during the final 10% (or alternatively, 20%, 30%, 40%, 50%) of an exhalation phase. In the context of this disclosure, "substantially constant" may mean having fluctuations or variations not to exceed a small predetermined relative range, such as 5% of the current pressure or 10% of the current pressure, or not to exceed a small predetermined absolute range, such as 1 cmH$_2$O or 2 cmH$_2$O.

As was described above, control module 113 may be configured to adjust pressure levels of the pressurized flow of breathable gas such that, for a comparison spanning a given duration of time and/or number of breaths, exhalation pressure levels are generally higher than inhalation pressure levels. By way of illustration, FIG. 4 illustrates a pressure profile 42, plotting mask pressure 6 over time, in which the inhalation (mask) pressure during inhalation phases 2 is lower, on average, than the exhalation (mask) pressure during exhalation phases 3. Transitional moment 4 separates an inhalation phase 2 from a subsequent exhalation phase 3. Transitional moment 5 separates an exhalation phase 3 from a subsequent inhalation phase 2. For reference, pressure profile 41 in FIG. 4 illustrates a typical CPAP prescription, with pressure generator 140 providing a constant pressure level of 10 cmH$_2$O throughout the breathing cycle. Note that the exhalation pressure 43 at the end of the exhalation phase is elevated, by an elevation 45 of approximately 2 cmH$_2$O, compared to pressure profile 41. The inhalation pressure following such an elevation (at lowest inhalation pressure level 44 during a given inhalation phase) may be significantly reduced (compared to pressure profile 41), possibly to zero cmH$_2$O or below, without an occurrence of an airway collapse and/or sleep apnea. Compared to pressure profile 41, pressure profile 42 is thought to represent a significantly more comfortable and/or natural way to breathe, overall, for a subject using airway pressure therapy.

Figure 5:
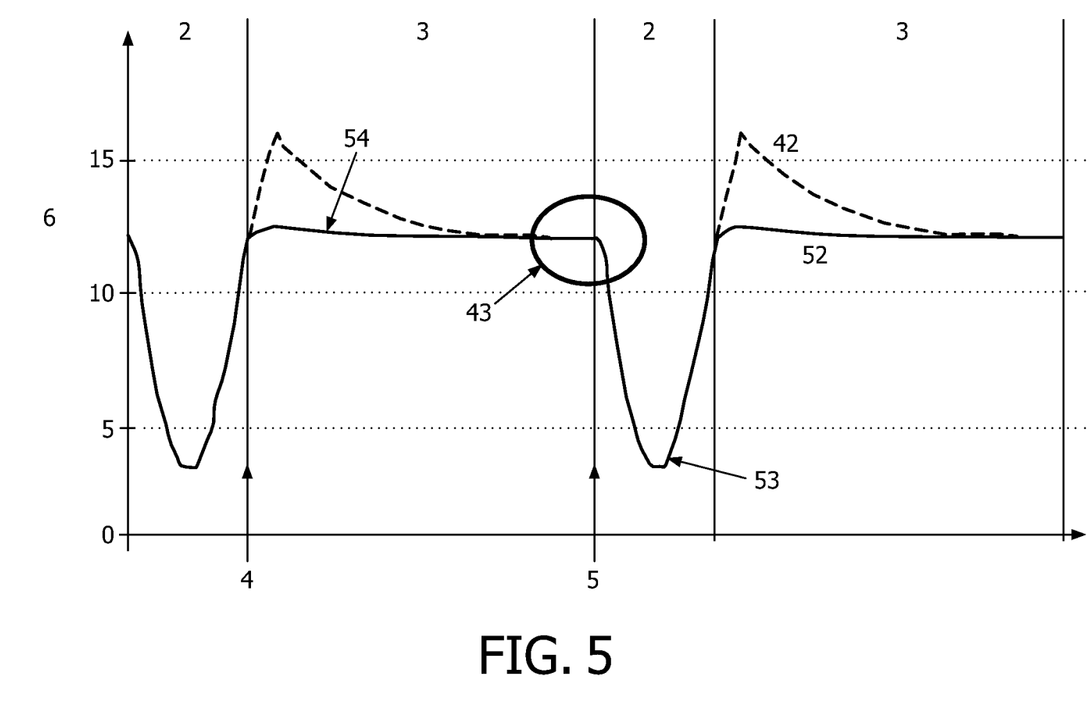

Referring to pressure profile 42 of FIG. 4, note the pressure increase (a.k.a. a pressure peak) during the first part of exhalation phase 3. This pressure peak may be prevented if control of pressure generator 140 accounts for the resistance of subject interface 180 and/or conduit 182. In particular when using a restrictive flow hose as described above—having a higher resistance—a pressure peak may occur. By way of illustration, FIG. 5 illustrates a pressure profile 52 thus characterized, having a non-significant pressure peak 54, which may be more comfortable for subject 106. While the lowest inhalation pressure 53 may be slightly higher than inhalation pressure 44 in FIG. 4, exhalation pressure 43 remains similar to or the same as it was in FIG. 4. Anticipating the flow demand of subject 106, as shown in FIG. 5, may reduce the drop, compared to pressure profile 42, in mask pressure during an inhalation phase.

Figure 6:
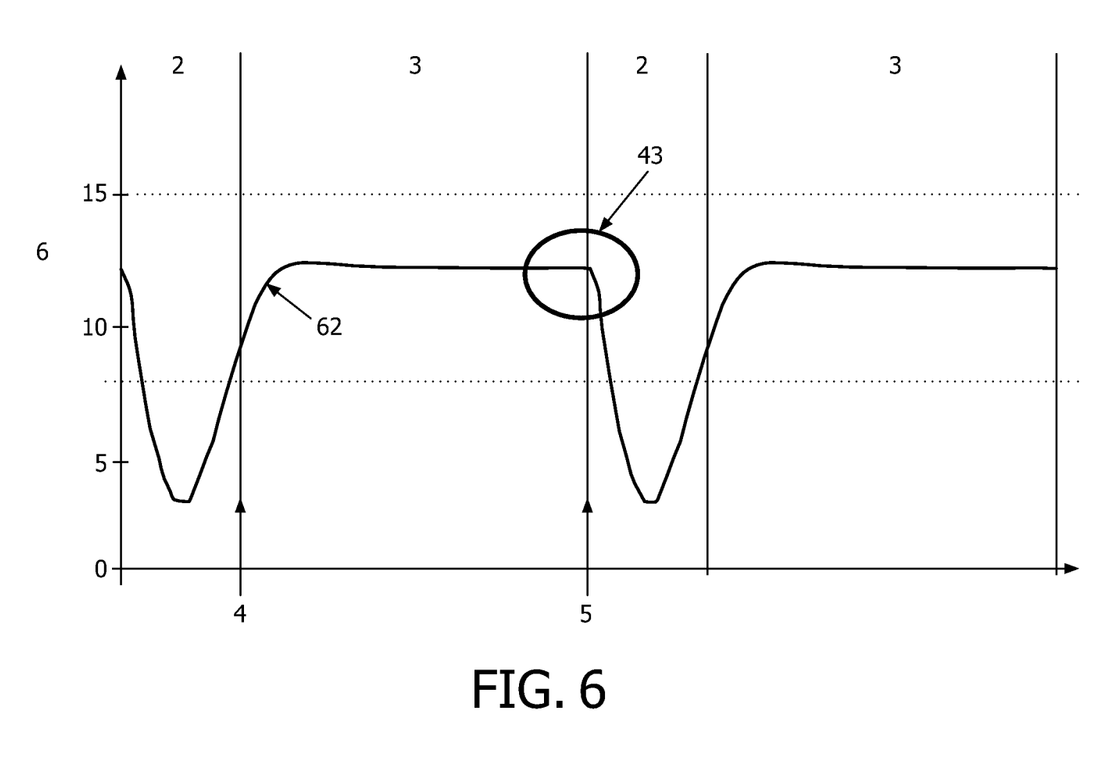

Control module 113 may be configured to adjust the rate of pressure level change during inhalation phases and exhalation phases. The rate of pressure level change, in particular from the lowest inhalation pressure level during a given inhalation phase to the highest exhalation pressure level during a subsequent exhalation phase that immediately follows the given inhalation phase, is a characteristic measurement of a pressure profile. Another characteristic measurement is the relative timing of the halfway point between these two levels. Control module 113 may be configured to adjust pressure, flow and/or resistance levels in order to achieve a particular rate of pressure level change, or, in coordination with timing module 111, achieve where in an inhalation phase or exhalation phase the halfway point between these two levels occurs. For example, it may be more comfortable for a subject to experience a more gradual change of pressure level, such as pressure profile 62 in FIG. 6, compared to pressure profile 52 in FIG. 5. Comparatively, the rate of pressure level change is lower, and the halfway point is delayed to be at or near transitional moment 4.

Figure 7:
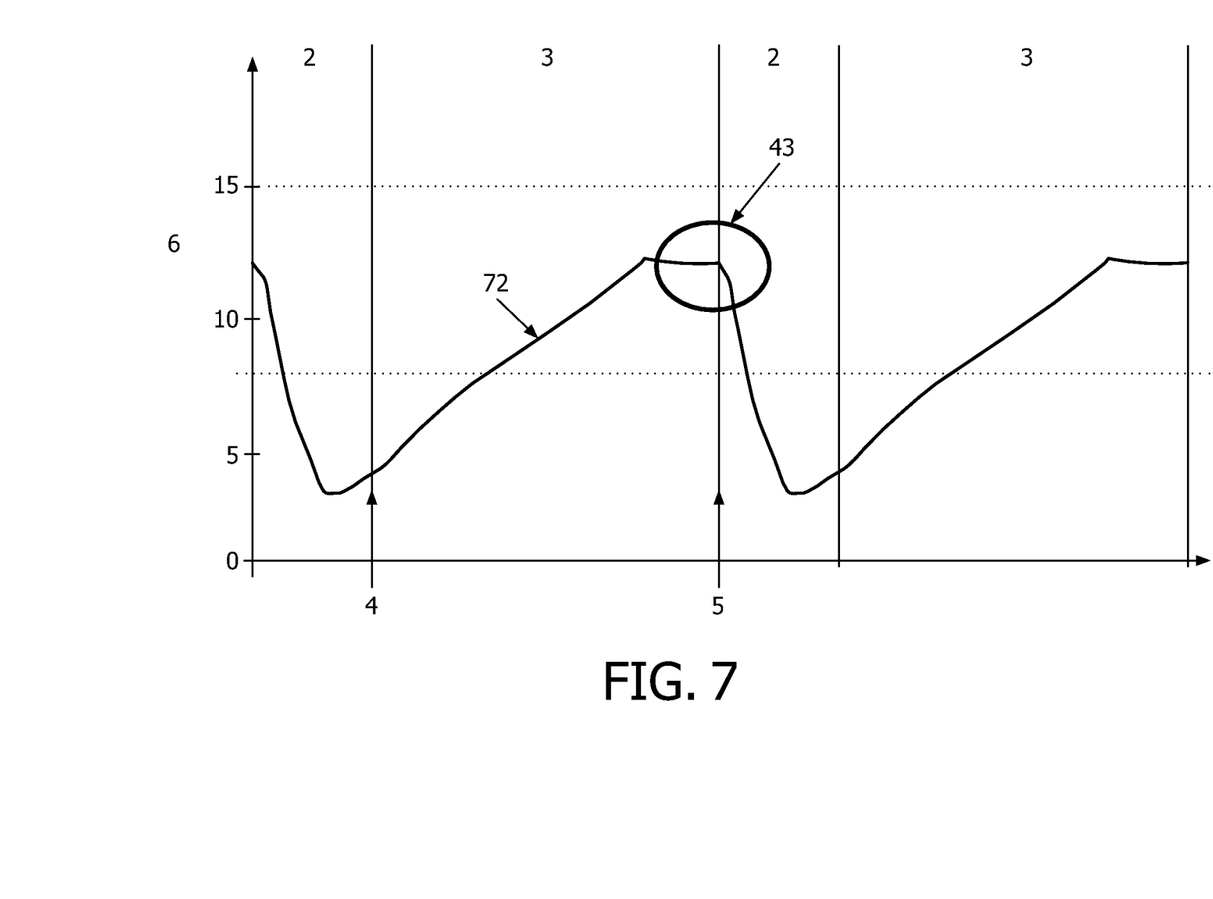

As another example, FIG. 7 illustrates a pressure profile 72 characterized by an even more gradual rate of pressure level change, and an even further delayed halfway point, which may occur at least 1.5 seconds, 2.0 seconds, 2.5 seconds, or 3.0 seconds after transitional moment 4. Note that the exhalation pressure in pressure profile 72 increases, e.g. monotonically, throughout at least the first half of the given exhalation phase. In spite of altering one or both of the afore-mentioned characteristic measurements of a pressure profile, the examples of FIGS. 5, 6, 7 all illustrate a similar elevation 45 of exhalation pressure 43 at the end of an exhalation phase, compared to pressure profile 41.

Control module 113 may be configured to adjust pressure levels to transition (gradually) between a traditional pressure profile, such as pressure profile 41 in FIG. 4, and, e.g., pressure profile 73 in FIG. 7, and/or vice versa. The demands, requirements, or needs of a subject may change through one or more respiratory therapy sessions.

Respiratory event module 114 is configured to detect occurrence of respiratory events, e.g. based on output signals generated by sensor 142 and/or parameters determined by parameter determination module 112. For example, respiratory event module 114 can detect occurrences of Cheyne-Stokes respiration, central sleep apneas, obstructive sleep apneas, hypopneas, snoring, hyperventilation, and/or other respiratory events. Such an occurrence may be used to alter the operating parameters of other constituent components of system 100. For example, system 100 may use an elevation 45 of 1.5 cmH$_2$O to treat sleep apnea, when respiratory event module 114 detects an occurrence of an obstructive sleep apnea. In response to this detection, control module 113 may adjust the pressure profile to use an elevation of 2.0, 2.5, 3.0 cmH$_2$O, or another level of elevation.

System 100 may comprise standard CPAP equipment, using a standard size hose, but with a flow resistor added at either end of the conduit and/or subject interface. Even though the hose is larger, the added resistance (for example, as a part of an adapter kit), plus the use of a mask with the valve and exhalation resistance described elsewhere in this detailed description, may convert a standard CPAP system to a system capable of operation in accordance with the description provided herein.

In some embodiments, a standard CPAP, mask, and hose may be used without adaptation, but with special programming to provide mask pressure profiles described elsewhere in this description. This may be implemented as one of multiple therapy modes programmed into a CPAP, thus offering a therapy option for the patient and physician to use. In such an embodiment, using a standard CPAP, mask, and hose, with programming that provides the pressure profiles of this invention, a subject may re-breathe more carbon-dioxide compared to a previously described system using a limited flow hose, which may assist a treatment for central apneas or Cheyne-Stokes respiration.

Figure 8:
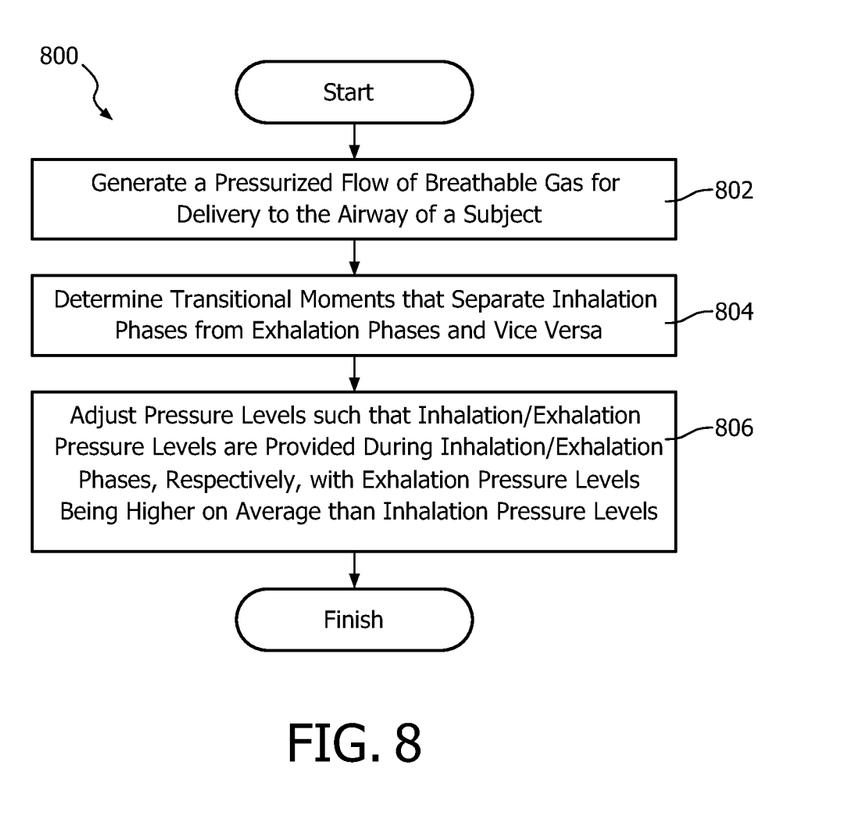
FIG. 8 illustrates a method for treating sleep apnea of a subject.

FIG. 8 illustrates a method 800 for treating central sleep apnea of a subject. The operations of method 800 presented below are intended to be illustrative. In certain embodiments, method 800 may be accomplished with one or more additional operations not described, and/or without one or more of the operations discussed. Additionally, the order in which the operations of method 800 are illustrated in FIG. 8 and described below is not intended to be limiting.

In certain embodiments, method 800 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 800 in response to instructions stored electronically on an electronic storage medium. The one or more processing devices may include one or more devices configured through hardware, firmware, and/or software to be specifically designed for execution of one or more of the operations of method 800.

At an operation 802, a pressurized flow of breathable gas is generated for delivery to the airway of a subject. In one embodiment, operation 802 is performed by a pressure generator similar to or substantially the same as pressure generator 140 (shown in FIG. 1 and described above).

At an operation 804, transitional moments are determined that separate inhalation phases from exhalation phases and/or vice versa. In one embodiment, operation 804 is performed by a timing module similar to or substantially the same as timing module 111 (shown in FIG. 1 and described above).

At an operation 804, pressure levels are adjusted such that inhalation/exhalation pressure levels are provided during inhalation/exhalation phases, respectively. The adjustments are controlled such that the average exhalation pressure level is higher than the average inhalation pressure level. In one embodiment, operation 804 is performed by a control module similar to or substantially the same as control module 113 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the embodiments have been described in detail for the purpose of illustration based on what is currently considered to be most practical and preferred, it is to be understood that such detail is solely for that purpose and does not impose any limits, but, on the contrary, the disclosure is intended to cover modifications and equivalent arrangements that are within the spirit and scope of the appended claims. For example, it is to be understood that, to the extent possible, one or more features of any embodiment are contemplated to be combined with one or more features of any other embodiment.

The invention claimed is:

1. A system for treating sleep disordered breathing of a subject having an airway, the system comprising:
   a pressure generator configured to generate a pressurized flow of breathable gas for delivery to the airway of the subject via one or more gas delivery components; and
   one or more processors configured to execute computer program modules, the computer program modules comprising:
   a timing module configured to determine transitional moments that separate inhalation phases from exhalation phases and/or vice versa; and
   a control module configured to control the pressure generator to adjust pressure levels of the pressurized flow of breathable gas, wherein the control module is configured to control the pressure generator to provide the pressurized flow of breathable gas at inhalation pressure levels during inhalation phases, and to provide the pressurized flow of breathable gas at exhalation pressure levels during exhalation phases, wherein:
      an average of the exhalation pressure levels of the pressurized flow of breathable gas provided to the subject from the pressure generator is higher than a prescribed constant positive airway pressure therapy pressure level, and an average of the inhalation pressure levels of the pressurized flow of breathable gas provided to the subject from the pressure generator is lower than the prescribed constant positive airway pressure therapy pressure level.

2. The system of claim 1, wherein the control module is further configured such that a given exhalation pressure level for a given exhalation phase steadily increases in a ramped manner throughout at least the first 10% of the given exhalation phase.

3. The system of claim 1, wherein the control module is further configured such that the pressure levels of the pressurized flow of breathable gas increase from the lowest inhalation pressure level during a given inhalation phase to the highest exhalation pressure level during a subsequent exhalation phase that immediately follows the given inhalation phase in a ramped manner over a ramping period spanning at least 50% of a combined duration of the given inhalation phase and the subsequent exhalation phase.

4. The system of claim 1, wherein the control module is further configured such that: (1) a given inhalation pressure level is 0 cmH2O or less, and (2) a given exhalation pressure level is substantially constant throughout a predetermined period within a given exhalation phase, wherein the predetermined period comprises about a final 10% of the given exhalation phase, and wherein the given exhalation pressure level is elevated from the reference sleep disorder breathing constant positive airway pressure therapy pressure levels by at least 0.5 cmH2O.

5. The system of claim 1, wherein the prescribed constant positive airway pressure therapy pressure level is 10 cmH$_2$O and wherein the average of the exhalation pressure levels is higher than the prescribed constant positive airway pressure therapy pressure level by approximately 2 cmH$_2$O.

6. The system of claim 1, wherein the control module is configured such that the average of the exhalation pressure levels is higher than the prescribed constant positive airway pressure therapy pressure level by a first treatment amount of pressure, and responsive to detection of an occurrence of a respiratory event in the subject, the average of the exhalation pressure levels is higher than the prescribed constant positive airway pressure therapy pressure level by a second increased treatment amount of pressure relative to the first treatment amount of pressure.

7. The system of claim 1, further comprising:
a subject interface configured to place the pressure generator in fluid communication with the subject, wherein the subject interface includes a flow resistor,
wherein the control module is configured to control the pressure generator to adjust pressure levels of the pressurized flow of breathable gas such that resistance of the flow resistor and resistance of the one or more gas delivery components are both taken into account to prevent occurrence of a pressure peak during a first portion of a given exhalation phase relative to exhalation pressures during a second portion of the given exhalation phase.

8. The system of claim 7, wherein the one or more gas delivery components include a 6 mm-9 mm diameter limited flow hose having a greater resistance to gas flow than a 22 mm diameter size hose.

9. A system configured to treat sleep disorder breathing of a subject having an airway, the system comprising:
means for generating a pressurized flow of breathable gas for delivery to the airway of the subject;
means for delivering breathable gas to the airway of the subject;
means for determining transitional moments that separate inhalation phases from exhalation phases and/or vice versa; and
means for adjusting pressure levels of the pressurized flow, such that inhalation pressure levels are provided during inhalation phases and exhalation pressure levels are provided during exhalation phases, wherein:
an average of the exhalation pressure levels of the pressurized flow of breathable gas provided to the subject from the means for generating the pressurized flow of breathable gas is higher than a prescribed constant positive airway pressure therapy pressure level, and
an average of the inhalation pressure levels of the pressurized flow of breathable gas provided to the subject from the means for generating the pressurized flow of breathable gas is lower than the prescribed constant positive airway pressure therapy pressure level.

10. The system of claim 9, wherein operation of the means for adjusting pressure levels of the pressurized flow includes steadily increasing a given exhalation pressure level in a ramped manner for a given exhalation phase throughout at least the first 10% of the given exhalation phase.

11. The system of claim 9, further comprising:
means for placing the means for generating a pressurized flow of breathable gas in fluid communication with the subject, including a means for increasing flow resistance;
wherein the means for adjusting pressure levels of the pressurized flow takes into account both a resistance of the means for increasing flow resistance and a resistance of the means for delivering breathable gas to the airway of the subject to prevent occurrence of a pressure peak during a first portion of a given exhalation phase relative to exhalation pressures during a second portion of the given exhalation phase.

12. The system of claim 9, wherein operation of the means for adjusting pressure levels of the pressurized flow includes increasing a pressure level of the pressurized flow of breathable gas from the lowest inhalation pressure level during a given inhalation phase to the highest exhalation pressure level during a subsequent exhalation phase that immediately follows the given inhalation phase in a ramped manner such that the pressure level increases over a ramping period spanning at least 50% of a combined duration of the given inhalation phase and the subsequent exhalation phase.

13. The system of claim 9, wherein operation of the means for adjusting pressure levels of the pressurized flow includes: (1) controlling a given inhalation pressure during a given inhalation phase such that the given inhalation pressure is 0 cmH2O or less, and (2) controlling a given exhalation pressure during a given exhalation phase such that the given exhalation pressure is substantially constant throughout a predetermined period within the given exhalation phase, wherein the predetermined period comprises about a final 10% of the given exhalation phase, and wherein the given exhalation pressure level is elevated from the reference sleep disorder breathing constant positive airway pressure therapy pressure levels by at least 0.5 cmH2O.

14. The system of claim 9, wherein the prescribed constant positive airway pressure therapy pressure level is 10 cmH$_2$O and wherein the average of the exhalation pressure levels is higher than the prescribed constant positive airway pressure therapy pressure level by approximately 2 cmH$_2$O.

15. The system of claim 9, wherein the means for adjusting is configured such that the average of the exhalation pressure levels is higher than the prescribed constant positive airway pressure therapy pressure level by a first treatment amount of pressure, and responsive to detection of an occurrence of a respiratory event in the subject, the average of the exhalation pressure levels is higher than the prescribed constant positive airway pressure therapy pressure level by a second increased treatment amount of pressure relative to the first treatment amount of pressure.

\* \* \* \* \*